US007414031B2

(12) United States Patent
Keicher et al.

(10) Patent No.: US 7,414,031 B2
(45) Date of Patent: Aug. 19, 2008

(54) 5-NITRO-NUCLEOSIDE COMPOUNDS FOR TREATING VIRAL INFECTIONS

(75) Inventors: Jesse D. Keicher, Menlo Park, CA (US); Christopher D. Roberts, Belmont, CA (US); Natalia B. Dyatkina, Mountain View, CA (US)

(73) Assignee: Genelabs Technologies, Inc., Redwood City, CA (US)

( * ) Notice: Subject to any disclaimer, the term of this patent is extended or adjusted under 35 U.S.C. 154(b) by 279 days.

(21) Appl. No.: 11/280,984

(22) Filed: Nov. 15, 2005

(65) Prior Publication Data

US 2006/0111311 A1 May 25, 2006

Related U.S. Application Data

(60) Provisional application No. 60/630,453, filed on Nov. 22, 2004.

(51) Int. Cl.
*A61K 31/70* (2006.01)
*C07H 19/14* (2006.01)

(52) U.S. Cl. .................. 514/43; 536/26.23; 536/26.26; 536/26.7; 536/27.2

(58) Field of Classification Search ........................ None
See application file for complete search history.

(56) References Cited

U.S. PATENT DOCUMENTS

| 4,107,288 | A | 8/1978 | Oppenheim et al. | |
|---|---|---|---|---|
| 5,145,684 | A | 9/1992 | Liversidge et al. | |
| 5,597,691 | A | 1/1997 | Houghton et al. | |
| 5,738,985 | A | 4/1998 | Miles et al. | |
| 5,739,002 | A | 4/1998 | De Francesco et al. | |
| 5,759,795 | A | 6/1998 | Jubin | |
| 5,861,267 | A | 1/1999 | Su | |
| 6,030,785 | A | 2/2000 | Katze et al. | |
| 6,228,576 | B1 | 5/2001 | Delvecchio | |
| 6,777,395 | B2 * | 8/2004 | Bhat et al. ................. | 514/43 |
| 7,105,499 | B2 * | 9/2006 | Carroll et al. ............... | 514/49 |
| 7,125,855 | B2 * | 10/2006 | Bhat et al. ................. | 514/43 |
| 7,202,224 | B2 * | 4/2007 | Eldrup et al. ................ | 514/43 |
| 2005/0090463 | A1 | 4/2005 | Roberts et al. | |
| 2006/0079468 | A1 | 4/2006 | Roberts et al. | |

FOREIGN PATENT DOCUMENTS

| WO | WO 97/12033 A1 | 4/1997 |
|---|---|---|
| WO | WO 01/90121 A2 | 11/2001 |
| WO | WO 02/18404 A2 | 3/2002 |
| WO | WO 02/057287 A2 | 7/2002 |
| WO | WO 02/057425 A2 | 7/2002 |
| WO | WO 03/061385 A1 | 7/2003 |
| WO | WO 03/061576 A2 | 7/2003 |
| WO | WO 2004/007512 A2 | 1/2004 |
| WO | WO 2004/028481 A2 | 4/2004 |
| WO | WO 2005/021568 A2 | 3/2005 |
| WO | WO 2005/042556 A1 | 5/2005 |

OTHER PUBLICATIONS

Cooperwood, J. S., et al., "Nucleoside and Nucleotide prodrugs" in Ed(s) Chu, C. K. Recent Advances in Nucleosides 2002, 92-147.
Ding, et al. "Synthesis of 2'-beta-C-methyl toyocamycin and sangivamycin analogues as potential HCV inhibitors" Bioorganic & Medicinal Chemistry Letters, 15(3):725-727, Feb. 2005.
Ferrari, et al., "Characterization of soluble hepatitis C virus RNA-dependent RNA polymerase expressed in *Escherichia coli*" J. Viro., 1999, 73, 1649-54.
Hinshaw, et al. "Pyrrolopyrimidine nucleosides. IV. Synthesis of certain 4, 5-disubstituted-7-(beta-D-ribofuranosyl)pyrrolo[2,3-d]pyrimidines related to the pyrrolo[2,3-d] pyrimidine nucleoside antibiotics" J. of Heterocyclic Chemistry 1969, 6(2):215-221.
Hinshaw, et al. "Pyrrolopyrimidine nucleosides. Part X. Synthesis of certain 4,5-disubstituted 7-(beta-D-ribofuranosyl)pyrrolo[2,3-d]pyrimidines related to toyocamycin and sangivamycin" J. of the Chemical Society, Perkin Transactions: Organic and Bio-Organic Chemistry 1975 13, 1248-53.
Hutchinson, D.W. (Ed. Leroy B. Townsend) "The Synthesis, Reaction and Properties of Nucleoside Mono-, Di-, Tri-, and Tetraphosphates and Nucleosides with Changes in the Phosphoryl Residue" Chemistry of Nucleosides and Nucleotides, Plenum Press, (1991) 2.
Ishii, et al., "Expression of hepatitis C virus NS5B protein: characterization of its RNA polymerase activity and RNA binding." Hepatology, 1999, 29, 1227-35.
Lohmann, et al., "Replication of subgenomic hepatitis C virus RNAs in a hepatoma cell line." Science, 1999, 285, 110-13.
Lohmann, et al., "Selective Stimulation of Hepatitis C Virus and Pestivirus NS5B RNA Polymerase Activity by GTP." J. Bio. Chem., 1999, 274, 10807-15.
Mandal, S.B., et al., "Stereospecific C-β-glycosidation and synthesis of 4,7-anhydro-5,6-isopropylidene-4(S), 5(S), 6(R), 7(R)-tetrahydroxyoxocan-2-one" Synth. Commun., 1993, 9, 1239.
Meier, C., "Pro-Nucleotides—recent advances in the design of efficient tools for the delivery of biologically active nucleoside monophosphates" Synlett 1998, 3, 233-42.
Ning, J., et al., "Syntheses and reactions of 5-O-acetyl-1,2-anhydro-3-O-benzyl-alpha-D-ribofuranose and beta-D-lyxofuranose, 5-O-acetyl-1,2-anhydro-3,6-di-O-benzyl- and 1,2-anhydro-5,6-di-O-benzoyl-3-O-benzyl-beta-D-mannofuranose, and 6-O-acetyl-1,2-anhydro-3,4-di-O-benzyl-alpha-D-glucopyranose and—beta-D-talopyranose," Carbohydr. Res., 2001, 330, 165-75.
Saunders and Raybuck, "Inosine Monophosphate Dehydrogenase: Consideration of Structure, Kinetics and Therapeutic Potential." Ann. Rep. Med. Chem., 2000, 35, 201-10.
Seela, et al., "7-substituted-7-deaza-2'-deoxyadenosines and 8-aza-7-deaza-2'-deoxyadenosines: fluorescence of DNA-base analogues induced by the 7-alkynyl side chain" Helvetica Chimica Acta, 2000 83(5), 910-927.

(Continued)

*Primary Examiner*—L. E. Crane
(74) *Attorney, Agent, or Firm*—Foley & Lardner LLP; Junrui Yang

(57) ABSTRACT

Disclosed are compounds, compositions and methods for treating viral infections caused by a flaviviridae family virus, such as hepatitis C virus.

3 Claims, No Drawings

OTHER PUBLICATIONS

Wagner, C., et al., "Pronucleotides: Toward the in vivo delivery of antiviral and anticancer nucleotides." Medicinal Research Reviews 2000, 20(6), 417-451.

Witty, D.R., et al., "Ring contraction of 2-o-trifluoromethanesulphonates of α-hydroxy-γ-lactones to oxetane carboxylic esters." Tet. Lett., 1990, 31, 4787.

Yamashita, et al., "RNA-dependent RNA Polymerase Activity of the Soluble Recombinant Hepatitis C Virus NS5B Protein Truncated at the C-terminal Region," J. Bio. Chem., 1998, 273, 15479-86.

Zemlicka, J., et al., "Lipophilic phosphoramidates as antiviral pronucleotides." Biochimica et Biophysica Acta 2002, 158(2-3), 276-286.

* cited by examiner

5-NITRO-NUCLEOSIDE COMPOUNDS FOR TREATING VIRAL INFECTIONS

CROSS-REFERENCE TO RELATED APPLICATIONS

This application claims the benefit under 35 U.S.C. §119 (e) from U.S. Provisional Patent Application Ser. No. 60/630,453, filed Nov. 22, 2004, which application is incorporated herein by reference in its entirety.

FIELD OF THE INVENTION

The invention relates to the field of pharmaceutical chemistry, in particular to compounds, compositions and methods for treating viral infections in mammals mediated, at least in part, by a virus in the flaviviridae family of viruses.

REFERENCES

The following publications are cited in this application as superscript numbers:
1. Giangaspero, et al., Arch. Virol. Suppl., 7: 53-62 (1993);
2. Giangaspero, et al., Int. J. STD. AIDS, 4(5): 300-302 (1993);
3. Yolken, et al., Lancet, 1(8637): 517-20 (1989);
4. Wilks, et al., Lancet, 1(8629): 107 (1989);
5. Giangaspero, et al., Lancet, 2: 110 (1988);
6. Potts, et al., Lancet, 1(8539): 972-973 (1987);
7. Cornberg, et al., "Hepatitis C: therapeutic perspectives." Forum (Genova), 11(2):154-62 (2001);
8. Dymock, et al., Antivir. Chem. Chemother. 11(2):79-96 (2000);
9. Devos, et al., International Patent Application Publication No. WO 02/18404 A2, published 7 Mar. 2002;
10. Sommadossi, et al., International Patent Application Publication No. WO 01/90121, published 23 May 2001;
11. Carroll, S. S., et al., International Patent Application Publication No. WO 02057287, published 25 Jul. 2002;
12. Carroll, S. S., et al., International Patent Application Publication No. WO 02057425, published 25 Jul. 2002;
13. Roberts et al., U.S. patent application Ser. No. 10/861,090, filed Jun. 4, 2004, now U.S. Pat. No. 7,202,223.
14. Roberts et al., U.S. patent application Ser. No. 10/861,311, filed Jun. 4, 2004, now U.S. Pat. No. 7,144,868.

All of the above publications and applications are herein incorporated by reference in their entirety to the same extent as if each individual publication or application was specifically and individually indicated to be incorporated by reference in its entirety.

State of the Art

The Flaviviridae family of viruses is composed of three genera: pestivirus, flavivirus and hepacivirus (hepatitis C virus). Of these genera, flaviviruses and hepaciviruses represent important pathogens of man and are prevalent throughout the world. There are 38 flaviviruses associated with human disease, including the dengue fever viruses, yellow fever virus and Japanese encephalitis virus. Flaviviruses cause a range of acute febrile illnesses and encephalitic and hemorrhagic diseases. Hepaciviruses currently infect approximately 2 to 3% of the world population and cause persistent infections leading to chronic liver disease, cirrhosis, hepatocellular carcinoma and liver failure. Human pestiviruses have not been as extensively characterized as the animal pestiviruses. However, serological surveys indicate considerable pestivirus exposure in humans. Pestivirus infections in man have been implicated in several diseases including, but not likely limited to, congenital brain injury, infantile gastroenteritis and chronic diarrhea in human immunodeficiency virus (HIV) positive patients.[1-6]

Currently, there are no antiviral pharmaceutical drugs to prevent or treat pestivirus or flavivirus infections. For hepacivirus, i.e., hepatitis C virus (HCV) infections, interferon alpha (IFN) is currently the only approved drug in the United States. HCV is a major causative agent for post-transfusion and for sporadic non-A, non-B hepatitis. Infection by HCV is insidious in a high proportion of chronically infected (and infectious) carriers who may not experience clinical symptoms for many years.

At present, the only acceptable treatment for chronic HCV is interferon (IFN-alpha) and this requires at least six (6) months of treatment and/or Ribavirin, which can inhibit viral replication in infected cells and also improve liver function in some people.

IFN-alpha belongs to a family of naturally occurring small proteins with characteristic biological effects such as antiviral, immunoregulatory and antitumoral activities that are produced and secreted by most animal nucleated cells in response to several diseases, in particular viral infections. IFN-alpha is an important regulator of growth and differentiation affecting cellular communication and immunological control. Treatment of HCV with interferon, however, has limited long term efficacy with a response rate about 25%. In addition, treatment of HCV with interferon has frequently been associated with adverse side effects such as fatigue, fever, chills, headache, myalgias, arthralgias, mild alopecia, psychiatric effects and associated disorders, autoimmune phenomena and associated disorders and thyroid dysfunction.

Ribavirin (1-β-D-ribofuranosyl-1H-1,2,-4-triazole-3-carboxamide), an inhibitor of inosine 5'-monophosphate dehydrogenase (IMPDH), enhances the efficacy of IFN-alpha in the treatment of HCV. Despite the introduction of Ribavirin, more than 50% of the patients do not eliminate the virus with the current standard therapy of interferon-alpha (IFN) and Ribavirin. By now, standard therapy of chronic hepatitis C has been changed to the combination of PEG-IFN plus Ribavirin. However, a number of patients still have significant side effects, primarily related to Ribavirin. Ribavirin causes significant hemolysis in 10-20% of patients treated at currently recommended doses, and the drug is both teratogenic and embryotoxic.

Other approaches are being taken to combat the virus. They include, for example, application of antisense oligonucleotides or ribozymes for inhibiting HCV replication. Furthermore, low-molecular weight compounds that directly inhibit HCV proteins and interfere with viral replication are considered as attractive strategies to control HCV infection. NS3/4A serine protease, ribonucleic acid (RNA) helicase, RNA-dependent RNA polymerase are considered as potential targets for new drugs.[7,8]

Devos, et al.[9] describes purine and pyrimidine nucleoside derivatives and their use as inhibitors of HCV RNA replication. Sommadossi, et al.[10] describes 1',2' or 3'-modified nucleosides and their use for treating a host infected with HCV. Carroll, et al.[11,12], describes nucleosides as inhibitors of RNA-dependent RNA viral polymerase.

Recently, Roberts, et al.[13,14] disclosed that certain 7-(2'-substituted-β-D-ribofuranosyl)-4-amino-5-(optionally substituted ethyn-1-yl)-pyrrolo[2,3-d]pyrimidine compounds possess potent activity against HCV. These references are incorporated herein by reference in their entirety.

SUMMARY OF THE INVENTION

This invention is directed to novel compounds that are useful in the viral infections in mammals, mediated at least in part by a virus in the flaviviridae family of viruses. Specifically, the compounds of this invention are represented by Formula I below:

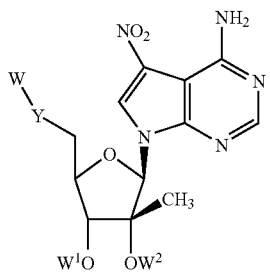

I wherein Y is selected from the group consisting of a bond, —CH$_2$— or —O—; and each of W, W$^1$ and W$^2$ is independently selected from the group consisting of hydrogen and a pharmaceutically acceptable prodrug;

or pharmaceutically acceptable salts or partial salts thereof.

Preferably each of W, W$^1$, and W$^2$ is independently hydrogen or a pharmaceutically acceptable prodrug selected from the group consisting of acyl, oxyacyl, phosphonate, phosphate esters, phosphate, phosphonamidate, phosphorodiamidate, phosphoramidate monoester, cyclic phosphoramidate, cyclic phosphorodiamidate, phosphoramidate diester, and —C(O)CHR$^3$NHR$^{13}$, where R$^3$ is selected from the group consisting of hydrogen, alkyl, substituted alkyl, aryl, substituted aryl, cycloalkyl, substituted cycloalkyl, heteroaryl, substituted heteroaryl, heterocyclic and substituted heterocyclic and a sidechain of an amino acid; or R$^3$ and R$^{13}$ together with the carbon and nitrogen atoms bound thereto respectively form a heterocyclic ring. Preferably, R$^{13}$ is H and R$^3$ and is a sidechain of an amino acid.

In a particularly preferred embodiment, the compounds of this invention are represented by Formula II below:

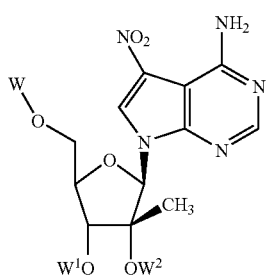

II

In Formula II, each of W, W$^1$ and W$^2$ is as defined above.

In still a further preferred embodiment, the compounds of this invention are represented by Formula III-XIII as follows wherein each of W, W$^1$ and W$^2$ is as defined above:

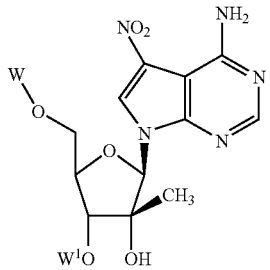

III

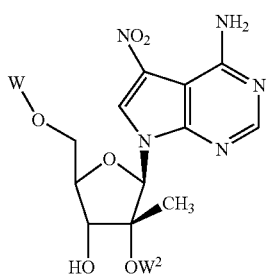

IV

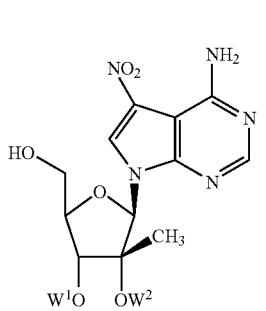

V

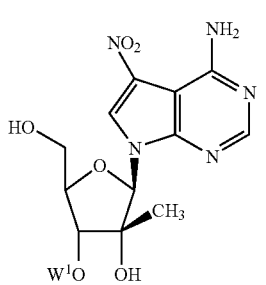

VI

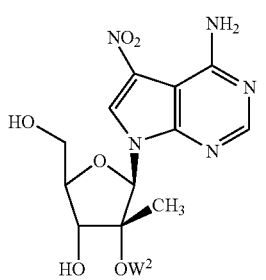

VII

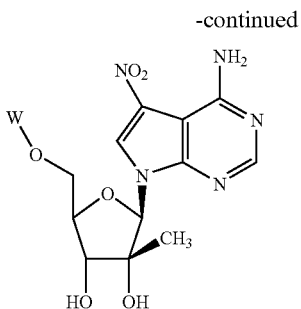

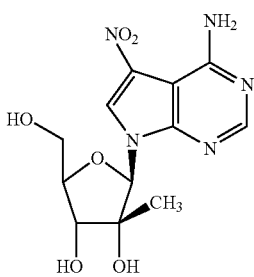

In another preferred embodiment W is hydrogen or a pharmaceutically acceptable prodrug selected from the group consisting of acyl, oxyacyl, phosphonate, phosphate esters, phosphate, phosphonamidate, phosphorodiamidate, phosphoramidate monoester, cyclic phosphoramidate, cyclic phosphorodiamidate, phosphoramidate diester, and —C(O)CHR$^3$NH$_2$.

In one particularly preferred embodiment, $W^1$ and $W^2$ are hydrogen and W is represented by the formula:

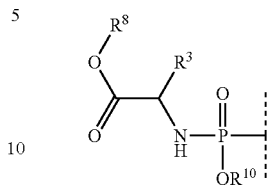

where $R^3$ is as defined above, $R^8$ is hydrogen or alkyl and $R^{10}$ is selected from the group consisting of alkyl, substituted alkyl, aryl, substituted aryl, cycloalkyl, substituted cycloalkyl, heteroaryl, substituted heteroaryl, heterocyclic and substituted heterocyclic. In a preferred embodiment $R^3$ is derived from an L-amino acid.

In another particularly preferred embodiment, W and $W^2$ are hydrogen and $W^1$ is represented by the formula:

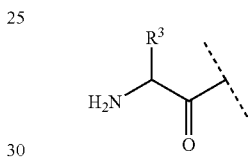

where $R^3$ is as defined above.

Particularly preferred compounds of this invention include those set forth in the following Table I (including pharmaceutically acceptable salts or partial salts thereof):

TABLE I

| # | Structure | Name |
|---|---|---|
| 101 | ![structure] | 7-(2'-C-methyl-β-D-ribofuranosyl)-4-amino-5-nitro-pyrrolo[2,3-d]pyrimidine |
| 102 | ![structure] | 7-(2'-C-methyl-5'-phospho-β-D-ribofuranosyl)-4-amino-5-nitro-pyrrolo[2,3-d]pyrimidine |

TABLE I-continued

| # | Structure | Name |
|---|---|---|
| 103 | (HO)₂P(O)OP(O)O— [ribose]—[7-NO₂, 4-NH₂ pyrrolopyrimidine]; OH on phosphate; 2'-C-methyl ribose with HO, OH | 7-(2'-C-methyl-5'-diphospho-β-D-ribofuranosyl)-4-amino-5-nitro-pyrrolo[2,3-d]pyrimidine |
| 104 | (HO)₂P(O)[OP(O)]₂O— [ribose]—[7-NO₂, 4-NH₂ pyrrolopyrimidine]; OH on phosphate; 2'-C-methyl ribose with HO, OH | 7-(2'-C-methyl-5'-triphospho-β-D-ribofuranosyl)-4-amino-5-nitro-pyrrolo[2,3-d]pyrimidine |

Compounds of this invention are active as antiviral agents or useful as intermediates in the preparation of antiviral agents of Formula I-IX.

This invention is also directed to pharmaceutical compositions comprising a pharmaceutically acceptable diluent and a therapeutically effective amount of a compound of Formula I-IX or mixtures of one or more of such compounds.

This invention is still further directed to methods for treating a viral infection mediated at least in part by a virus in the flaviviridae family of viruses, such as HCV, in mammals which methods comprise administering to a mammal, that has been diagnosed with said viral infection or is at risk of developing said viral infection, a pharmaceutical composition comprising a pharmaceutically acceptable diluent and a therapeutically effective amount of a compound of Formula I-IX or mixtures of one or more of such compounds.

In yet another embodiment of the invention, methods of treating or preventing viral infections in mammals are provided wherein the compounds of this invention are administered in combination with the administration of a therapeutically effective amount of one or more agents active against HCV. Active agents against HCV include Ribavirin, levovirin, viramidine, thymosin alpha-1, an inhibitor of NS3 serine protease, and inhibitor of inosine monophosphate dehydrogenase, interferon-alpha or pegylated interferon-alpha, either alone or in combination with Ribavirin or levovirin. Preferably the additional agent active against HCV is interferon-alpha or pegylated interferon-alpha alone or in combination with Ribavirin or levovirin.

DETAILED DESCRIPTION OF THE INVENTION

The invention is directed to compounds, compositions and methods for treating flaviviridae viruses, such as hepatitis C virus infections. However, prior to describing this invention in detail, the following terms will first be defined:

Definitions

As used herein, the term "alkyl" refers to alkyl groups having from 1 to 6 carbon atoms and more preferably 1 to 2 carbon atoms. This term is exemplified by groups such as methyl, ethyl, n-propyl, iso-propyl, n-butyl, t-butyl, n-pentyl and the like.

"Substituted alkyl" refers to an alkyl group having from 1 to 3, and preferably 1 to 2, substituents selected from the group consisting of alkoxy, substituted alkoxy, acyl, acylamino, acyloxy, oxyacyl, amino, substituted amino, aminoacyl, aryl, substituted aryl, aryloxy, substituted aryloxy, cyano, halogen, hydroxyl, nitro, carboxyl, carboxyl ester, cycloalkyl, substituted cycloalkyl, heteroaryl, substituted heteroaryl, heterocyclic, and substituted heterocyclic.

"Alkoxy" refers to the group "alkyl-O—" which includes, by way of example, methoxy, ethoxy, n-propoxy, iso-propoxy, n-butoxy, t-butoxy, sec-butoxy, n-pentoxy and the like.

"Substituted alkoxy" refers to the group "substituted alkyl-O—".

"Acyl" refers to the groups alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, aryl-C(O)—, substituted aryl-C(O)—, heteroaryl-C(O)—, substituted heteroaryl-C(O), heterocyclic-C(O)—, and substituted heterocyclic-C(O)—.

"Formyl" refers to the —C(O)H group.

"Acylamino" refers to the group —C(O)NR⁴R⁴ where each R⁴ is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where each R⁴ is joined to form together with the nitrogen atom a heterocyclic or substituted heterocyclic ring.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O—.

"Oxyacyl" refers to the groups alkyl-OC(O)—, substituted alkyl-OC(O)—, alkenyl-OC(O)—, substituted alkenyl-OC (O)—, alkynyl-OC(O)—, substituted alkynyl-OC(O)—, aryl-OC(O)—, substituted aryl-OC(O)—, cycloalkyl-OC(O)—, substituted cycloalkyl-OC(O)—, heteroaryl-OC(O)—, substituted heteroaryl-OC(O)—, heterocyclic-OC(O)—, and substituted heterocyclic-OC(O)—.

"Alkenyl" refers to alkenyl group having from 2 to 6 carbon atoms and preferably 2 to 4 carbon atoms and having at least 1 and preferably from 1-2 sites of alkenyl unsaturation. Such groups are exemplified by vinyl (ethen-1-yl), allyl, but-3-en-1-yl, and the like.

"Substituted alkenyl" refers to alkenyl groups having from 1 to 3 substituents, and preferably 1 to 2 substituents, selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl ester, cycloalkyl, substituted cycloalkyl, heteroaryl, substituted heteroaryl, heterocyclic, and substituted heterocyclic with the proviso that any hydroxyl substitution is not attached to a vinyl (unsaturated) carbon atom. Preferred substituted alkenyl groups are selected from, but not limit to, 2,2-difluoroethen-1-yl, 2-methoxyethen-1-yl, and the like.

It is understood that the terms "alkenyl" and "substituted alkenyl" includes both E (cis) and Z (trans) isomers as appropriate. The isomers can be pure isomeric compounds or mixtures of E and Z components.

"Alkynyl" refers to an unsaturated hydrocarbon having at least 1 site of alkynyl unsaturation and having from 2 to 6 carbon atoms and more preferably 2 to 4 carbon atoms. Preferred alkynyl groups are selected from but not limit to ethyn-1-yl, propyn-1-yl, propyn-2-yl, 1-methylprop-2-yn-1-yl, butyn-1-yl, butyn-2-yl, butyn-3-yl, and the like.

"Substituted alkynyl" refers to alkynyl groups having from 1 to 3 substituents, and preferably 1 to 2 substituents, selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl ester, cycloalkyl, substituted cycloalkyl, heteroaryl, substituted heteroaryl, heterocyclic, and substituted heterocyclic with the proviso that any hydroxyl substitution is not attached to an acetylenic carbon atom. Preferred substituted alkynyl groups are selected from but not limit to 2-fluoroethyn-1-yl, 3,3,3-trifluoropropyn-1-yl, 3-aminopropyn-1-yl, 3-hydroxypropyn-1-yl, and the like.

"Amino" refers to the group —$NH_2$.

"Substituted amino" refers to the group —NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where R' and R" are joined, together with the nitrogen bound thereto to form a heterocyclic or substituted heterocyclic group provided that R' and R" are both not hydrogen. When R' is hydrogen and R" is alkyl, the substituted amino group is sometimes referred to herein as alkylamino. When R' and R" are alkyl, the substituted amino group is sometimes referred to herein as dialkylamino.

"Aminoacyl" refers to the groups —$NR^5$C(O)alkyl, —$NR^5$C(O)substituted alkyl, —$NR^5$C(O)cycloalkyl, —$NR^5$C(O)substituted cycloalkyl, —$NR^5$C(O)alkenyl, —$NR^5$C(O)substituted alkenyl, —$NR^5$C(O)alkynyl, —$NR^5$C(O)substituted alkynyl, —$NR^5$C(O)aryl, —$NR^5$C(O)substituted aryl, —$NR^5$C(O)heteroaryl, —$NR^5$C(O)substituted heteroaryl, —$NR^5$C(O)heterocyclic, and —$NR^5$C(O)substituted heterocyclic where $R^5$ is hydrogen or alkyl.

"Aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is at an aromatic carbon atom. Preferred aryls include phenyl and naphthyl.

"Substituted aryl", including "substituted phenyl" refers to aryl groups or phenyl groups which are substituted with from 1 to 3 substituents, and preferably 1 to 2 substituents, selected from the group consisting of hydroxyl, acyl, acylamino, acyloxy, alkyl, substituted alkyl, alkoxy, substituted alkoxy, alkenyl, substituted alkenyl, alkynyl, substituted alkynyl, amino, substituted amino, aminoacyl, aryl, substituted aryl, aryloxy, substituted aryloxy, cycloalkoxy, substituted cycloalkoxy, carboxyl, carboxyl ester, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, halo, nitro, heteroaryl, substituted heteroaryl, heterocyclic, substituted heterocyclic, heteroaryloxy, substituted heteroaryloxy, heterocyclyloxy, and substituted heterocyclyloxy.

"Aryloxy" refers to the group aryl-O— that includes, by way of example, phenoxy, naphthoxy, and the like.

"Substituted aryloxy" refers to substituted aryl-O— groups.

"Carboxyl" refers to —COOH or salts thereof.

"Carboxyl ester" refers to the groups —C(O)O-alkyl, —C(O)O-substituted alkyl, —C(O)O-aryl, and —C(O)O-substituted aryl wherein alkyl, substituted alkyl, aryl and substituted aryl are as defined herein.

"Cycloalkyl" refers to cyclic alkyl groups of from 3 to 10 carbon atoms having single or multiple cyclic rings including, by way of example, adamantyl, cyclopropyl, cyclobutyl, cyclopentyl, cyclooctyl and the like.

"Substituted cycloalkyl" refers to a cycloalkyl having from 1 to 5 substituents selected from the group consisting of oxo (=O), thioxo (=S), alkyl, substituted alkyl, alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl ester, cycloalkyl, substituted cycloalkyl, heteroaryl, substituted heteroaryl, heterocyclic, and substituted heterocyclic.

"Cycloalkoxy" refers to —O-cycloalkyl groups.

"Substituted cycloalkoxy" refers to —O-substituted cycloalkyl groups.

"Halo" or "halogen" refers to fluoro, chloro, bromo and iodo and preferably is fluoro or chloro.

"Heteroaryl" refers to an aromatic group of from 1 to 10 carbon atoms and 1 to 4 heteroatoms selected from the group consisting of oxygen, nitrogen, sulfur in the ring. The sulfur and nitrogen heteroatoms atoms may also be present in their oxidized forms, such as >N(O), >S(O) and >$S(O)_2$. Such heteroaryl groups can have a single ring (e.g., pyridyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. Preferred heteroaryls include pyridyl, pyrrolyl, thienyl, indolyl, thiophenyl, and furyl.

"Substituted heteroaryl" refers to heteroaryl groups that are substituted with from 1 to 3 substituents selected from the same group of substituents defined for substituted aryl.

"Heteroaryloxy" refers to the group —O-heteroaryl and "substituted heteroaryloxy" refers to the group —O-substituted heteroaryl.

"Heterocycle" or "heterocyclic" or "heterocycloalkyl" refers to a saturated or unsaturated group (but not heteroaryl) having a single ring or multiple condensed rings, from 1 to 10 carbon atoms and from 1 to 4 hetero atoms selected from the group consisting of nitrogen, oxygen, sulfur, >S(O), and >S(O)$_2$ within the ring wherein, in fused ring systems, one or more of the rings can be cycloalkyl, aryl or heteroaryl provided that the point of attachment is through the heterocyclic ring.

"Substituted heterocyclic" or "substituted heterocycloalkyl" refers to heterocycle groups that are substituted with from 1 to 3 of the same substituents as defined for substituted cycloalkyl.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), piperidinyl, pyrrolidine, tetrahydrofuranyl, and the like.

"Heterocyclyloxy" refers to the group —O-heterocyclic and "substituted heterocyclyloxy" refers to the group —O-substituted heterocyclic.

"Phosphate" refers to the groups —OP(O)(OH)$_2$ (monophosphate or phospho), —OP(O)(OH)OP(O)(OH)$_2$ (diphosphate or diphospho) and —OP(O)(OH)OP(O)(OH)OP(O)(OH)$_2$ (triphosphate or triphospho) or salts thereof including partial salts thereof. It is understood, of course, that the initial oxygen of the mono-, di- and triphosphate (phospho, diphospho and triphospho) includes the oxygen atom at, for example, the 5-position of the ribose sugar.

"Phosphate esters" refers to the mono-, di- and tri-phosphate groups described above wherein one or more of the hydroxyl groups is replaced by an alkoxy group.

"Phosphonate" refers to the groups —OP(O)(R$^6$)(OH) or —OP(O)(R$^6$)(OR$^{6'}$) or salts thereof including partial salts thereof, wherein R$^6$ is independently selected from hydrogen, alkyl, and substituted alkyl, and R$^{6'}$ is independently selected from hydrogen, alkyl, substituted alkyl, carboxylic acid, and carboxyl ester. It is understood, of course, that the initial oxygen of the phosphonate includes the oxygen atom at, for example, the 5-position of the ribose sugar.

"Phosphorodiamidate" refers to the group:

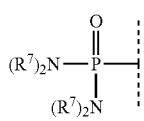

where each R$^7$ may be the same or different and each is hydrogen, alkyl, substituted alkyl, cycloalkyl, or substituted cycloalkyl. A particularly preferred phosphorodiamidate is the following group:

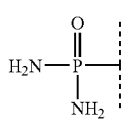

"Phosphoramidate monoester" refers to the group below, where R$^3$ is selected from the group consisting of hydrogen, alkyl, substituted alkyl, aryl, substituted aryl, cycloalkyl, substituted cycloalkyl, heteroaryl, substituted heteroaryl, heterocyclic and substituted heterocyclic and a sidechain of an amino acid; and R$^8$ is hydrogen or alkyl. In a preferred embodiment R$^3$ is derived from an L-amino acid.

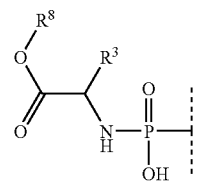

"Phosphoramidate diester" refers to the group below, where R$^{10}$ is selected from the group consisting of alkyl, substituted alkyl, aryl, substituted aryl, cycloalkyl, substituted cycloalkyl, heteroaryl, substituted heteroaryl, heterocyclic and substituted heterocyclic, and R$^3$ and R$^8$ are as defined above. In a preferred embodiment R$^3$ is derived from an L-amino acid.

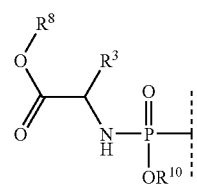

"Cyclic phosphoramidate" refers to the group below, where n is 1 to 3, more preferably n is 1 to 2.

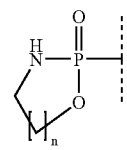

"Cyclic phosphorodiamidate" refers to the group below, where n is 1 to 3, more preferably n is 1 to 2.

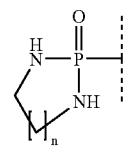

"Phosphonamidate" refers to the group below, where R$^{11}$ is hydrogen, alkyl, substituted alkyl, cycloalkyl, or substituted cycloalkyl.

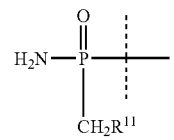

"Thiol" refers to the group —SH.

"Thioalkyl" or "alkylthioether" or "thioalkoxy" refers to the group —S-alkyl.

"Substituted thioalkyl" or "substituted alkylthioether" or "substituted thioalkoxy" refers to the group —S-substituted alkyl.

"Thiocycloalkyl" refers to the groups —S-cycloalkyl and "substituted thiocycloalkyl" refers to the group —S-substituted cycloalkyl.

"Thioaryl" refers to the group —S-aryl and "substituted thioaryl" refers to the group —S-substituted aryl.

"Thioheteroaryl" refers to the group —S-heteroaryl and "substituted thioheteroaryl" refers to the group —S-substituted heteroaryl.

"Thioheterocyclic" refers to the group —S-heterocyclic and "substituted thioheterocyclic" refers to the group —S-substituted heterocyclic.

The term "amino acid sidechain" refers to the $R^{3'}$ substituent of α-amino acids of the formula $R^{13}NHCH(R^{3'})COOH$ where $R^{3'}$ is selected from the group consisting of hydrogen, alkyl, substituted alkyl and aryl and $R^{13}$ is hydrogen or together with $R^{3'}$ and the nitrogen and carbon atoms bound thereto respectively form a heterocyclic ring. Preferably, the α-amino acid sidechain is the sidechain one of the twenty naturally occurring L-amino acids.

The term "pharmaceutically acceptable prodrugs" refers to art recognized modifications to one or more functional groups which functional groups are metabolized in vivo to provide a compound of this invention or an active metabolite thereof. Such functional groups are well known in the art including acyl groups for hydroxyl and/or amino substitution, esters of mono-, di- and tri-phosphates wherein one or more of the pendent hydroxyl groups have been converted to an alkoxy, a substituted alkoxy, an aryloxy or a substituted aryloxy group, and the like.

The term "pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkyl-ammonium, and the like; and when the molecule contains a basic functionality, salts of organic or inorganic acids, such as hydrochloride, hydrobromide, tartrate, mesylate, acetate, maleate, oxalate and the like.

The term "pharmaceutically acceptable partial salts" refers to compounds having a substituent capable of having more than one group form a salt but less than the maximum amount of such groups actually form a salt. For example, a diphospho group can form a plurality of salts and, if only partially ionized, the resulting group is sometimes referred to herein as a partial salt.

It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. In such cases, the maximum number of such substituents is three. That is to say that each of the above definitions is constrained by a limitation that, for example, substituted aryl groups are limited to -substituted aryl-(substituted aryl)-substituted aryl.

Similarly, it is understood that the above definitions are not intended to include impermissible substitution patterns (e.g., methyl substituted with 5 fluoro groups or a hydroxyl group alpha to ethenylic or acetylenic unsaturation). Such impermissible substitution patterns are well known to the skilled artisan.

General Synthetic Methods

The compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, *Protecting Groups in Organic Synthesis*, Third Edition, Wiley, New York, 1999, and references cited therein.

Furthermore, the compounds of this invention contain one or more chiral centers and such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures, or obvious modifications thereof, described in standard reference texts such as Fieser and Fieser's Reagents for Organic Synthesis, Volumes 1-15 (John Wiley and Sons, 1991), Rodd's Chemistry of Carbon Compounds, Volumes 1-5 and Supplementals (Elsevier Science Publishers, 1989), Organic Reactions, Volumes 1-40 (John Wiley and Sons, 1991), March's Advanced Organic Chemistry, (John Wiley and Sons, $4^{th}$ Edition), and Larock's Comprehensive Organic Transformations (VCH Publishers Inc., 1989). Specifically, the compounds of this invention may be prepared by various methods known in the art of organic chemistry in general and nucleoside and nucleotide analogue synthesis in particular. General reviews of the preparation of nucleoside and nucleotide analogues include 1) Michelson A. M. "*The Chemistry of Nucleosides and Nucleotides*," Academic Press, New York, 1963; 2) Goodman L. "*Basic Principles in Nucleic Acid Chemistry*," Academic Press, New York, 1974, vol. 1, Ch. 2; and 3) "*Synthetic Procedures in Nucleic Acid Chemistry*," Eds. Zorbach W. & Tipson R., Wiley, New York, 1973, vol. 1 & 2.

The synthesis of the compounds of this invention generally follows either a convergent or linear synthetic pathway as described below.

The strategies available for synthesis of compounds of this invention include for example:

General Synthesis of 2'-C-Branched Nucleosides

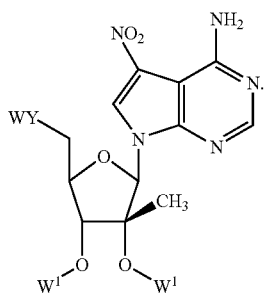

2'-C-Branched ribonucleosides of Formula I above, where Y, W, W$^1$, and W$^2$ are as defined above, can be prepared by one of the following general methods.

The 2'-C-substituted sugars used in the synthetic methods described herein are well known in the art and are described, for example, by Sommadossi, et al.[10] and by Carrol, et al.[11] both of which are incorporated herein by reference in their entirety.

Scheme 1 below describes the alternative synthesis of a protected sugar that is useful for coupling to the bases described herein.

Formation of sugar a in Scheme 1, above, is accomplished as described by Mandal, S. B., et al., *Synth. Commun.*, 1993, 9, page 1239, starting from commercial D-ribose. Protection of the hydroxyl groups to form sugar b is described in Witty, D. R., et al., *Tet. Lett.*, 1990, 31, page 4787. Sugar c and d are prepared using the method of Ning, J. et al., *Carbohydr. Res.*, 2001, 330, page 165, and methods described herein. Sugar e is prepared by using a modification of the Grignard reaction with CH$_3$MgBr or other appropriate organometallic as described herein (with no titanium/cerium needed). Finally the halogenated sugar (X=halo) used in the subsequent coupling reaction is prepared using the same protection method as used in to make sugar b above. The halogenation is described in Seela.[13]

Subsequently, any of the described nucleosides can be deprotected by methods well known to those skilled in the art, as taught by Greene et al. *Protective Groups in Organic Synthesis*, Jon Wiley and Sons, Second Edition, 1991.

An alternative approach to making protected sugars useful for coupling to heterocyclic bases is detailed in Scheme 2 below.

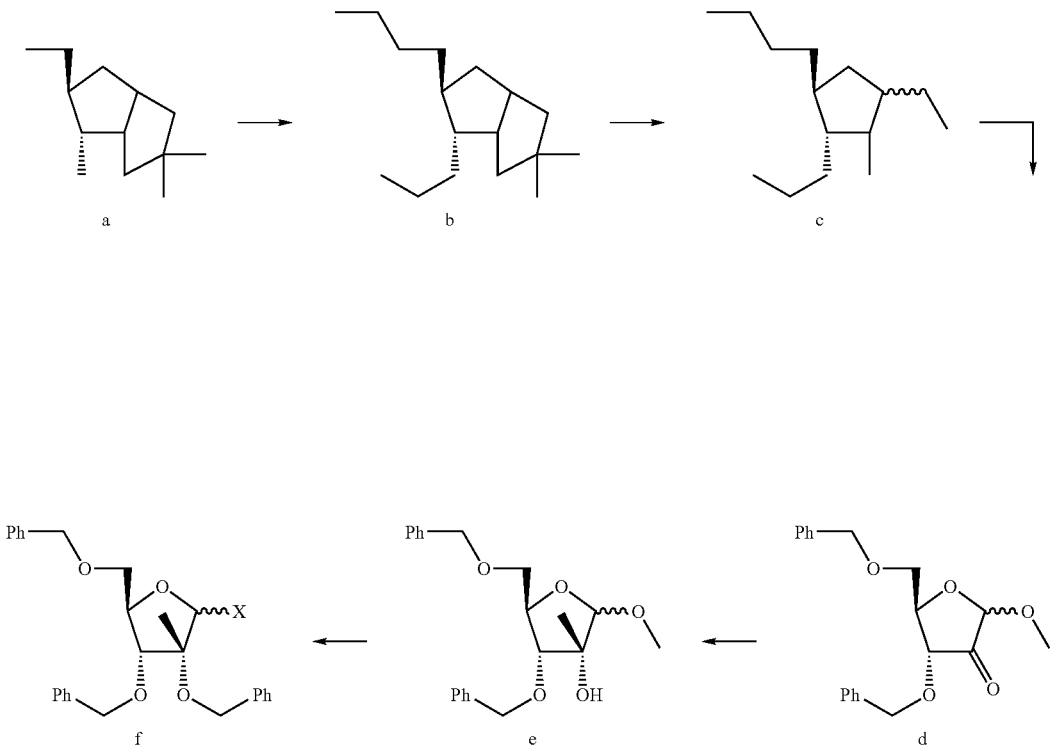

where Ph is phenyl and X is a suitable leaving group such as halo

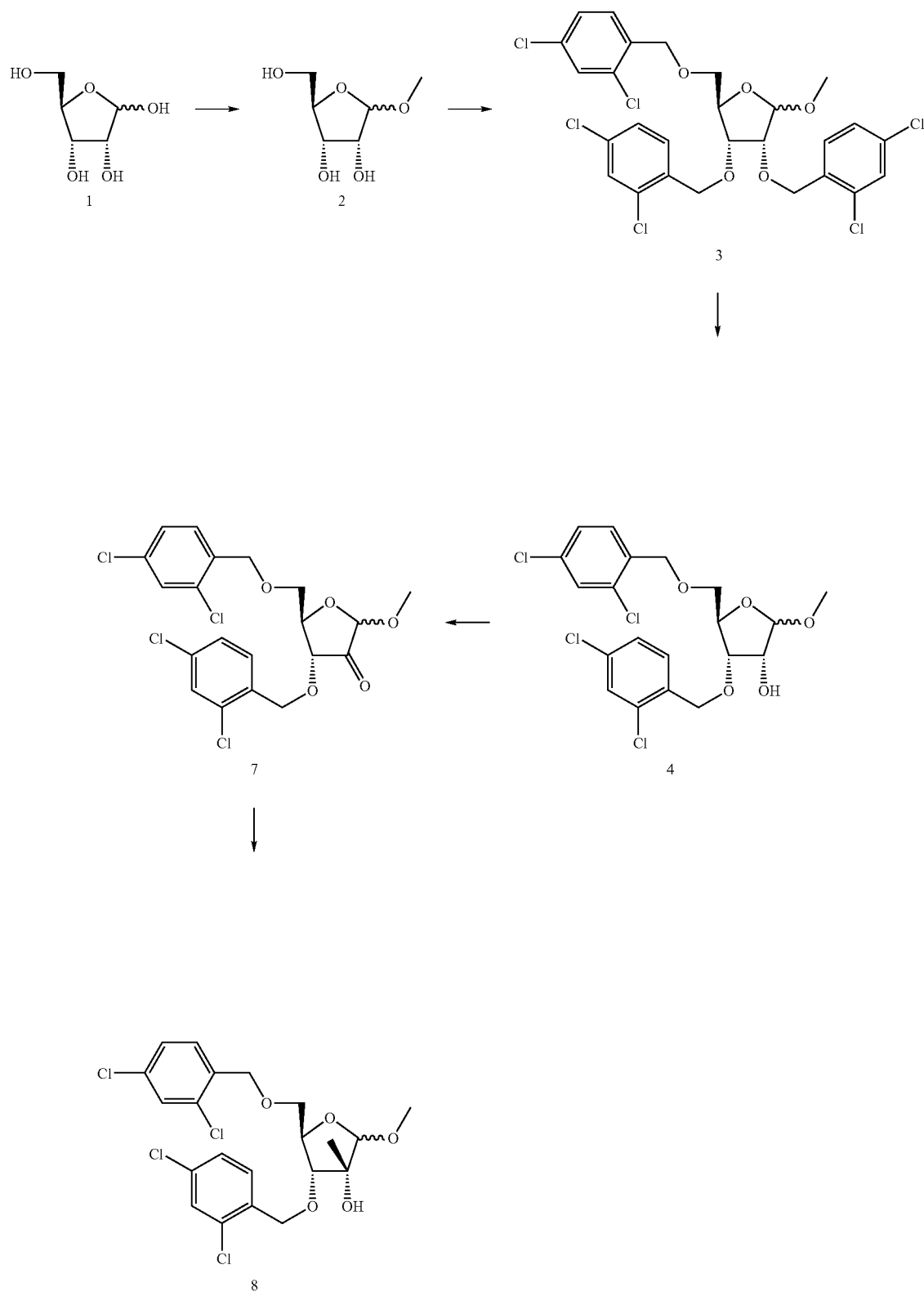

In Scheme 2, methylation of the hydroxyl group of compound 1 proceeds via conventional methodology to provide for compound 2. The 2, 3 and 5 hydroxyl groups of the compound 2 are each protected with 2,4-dichlorobenzyl groups to provide for compound 3. Selective deprotection of the 2-(2',4'-dichlorobenzyl) group on compound 3 proceeds via contact with stannous chloride in a suitable solvent such as methylene chloride, chloroform, and the like at reduced temperatures, e.g., ~0 to 5° C., until reaction completion, e.g., 24-72 hours. Oxidation of the 2-hydroxyl group proceeds as described herein to provide for compound 7. Methylation also proceeds as described herein to provide for compound 8.

In an alternative approach, an appropriately substituted nucleoside with a 2'-OH and 2'-H can be used as the starting material. This nucleoside can be purchased or can be prepared by any known means including standard coupling techniques. The nucleoside can be optionally protected with suitable protecting groups, preferably with acyl, substituted alkyl or silyl groups, by methods well known to those skilled in the art, as taught by Greene et al. *Protective Groups in Organic Synthesis*, John Wiley and Sons, Second Edition, 1991.

The hydroxyl group at the 2' position of the sugar of an otherwise appropriately protected nucleoside can then be oxidized with the appropriate oxidizing agent in a compatible solvent at a suitable temperature to yield the 2'-modified (oxo) sugar. Possible oxidizing agents are, for example, Dess-Martin periodine reagent, $Ac_2O+DCC$ in DMSO, Swern oxidation (DMSO, oxalyl chloride, triethylamine), Jones reagent (a mixture of chromic acid and sulfuric acid), Collins's reagent (dipyridine Cr(VI) oxide), Corey's reagent (pyridinium chlorochromate), pyridinium dichromate, acid dichromate, potassium permanganate, $MnO_2$, ruthenium tetroxide, phase transfer catalysts such as chromic acid or permanganate supported on a polymer, $Cl_2$-pyridine, $H_2O_2$-ammonium molybdate, $NaBrO_2$-CAN, NaOCl in HOAc, copper chromite, copper oxide, Raney nickel, palladium acetate, Meerwin-Pondorf-Verley reagent (aluminum t-butoxide with another ketone) and N-bromosuccinimide.

Coupling of an organometallic carbon nucleophile, such as a Grignard reagent, an organolithium, lithium dialkylcopper or $CH_3SiMe_3$ in TBAF (tetrabutyl-ammonium fluoride) with the ketone with the appropriate non-protic solvent at a suitable temperature, yields the alkyl substituted nucleoside. Isolation of the appropriate isomer is conducted as needed.

Subsequently, the nucleoside can be deprotected by methods well known to those skilled in the art, as taught by Greene et al. *Protective Groups in Organic Synthesis*, John Wiley and Sons, Second Edition, 1991.

In one embodiment of the invention, the D-enantiomers are utilized. However, L-enantiomers are also contemplated to be useful herein. The L-enantiomers corresponding to the compounds of the invention can be prepared following the same foregoing general methods, beginning with the corresponding L-sugar or nucleoside as starting material. In a particular embodiment, the 2'-C-branched ribonucleoside is desired.

The compounds of this invention may be prepared by various methods known in the art of organic chemistry in general and nucleoside and nucleotide analogue synthesis in particular. The starting materials for the syntheses are either readily available from commercial sources or are known or may be prepared by techniques known in the art. General reviews of the preparation of nucleoside and nucleotide analogues are included in the following:

Michelson A. M. "*The Chemistry of Nucleosides and Nucleotides*," Academic Press, New York, 1963.

Goodman L. "*Basic Principles in Nucleic Acid Chemistry*," Academic Press, New York, 1974, vol. 1, Ch. 2.

"*Synthetic Procedures in Nucleic Acid Chemistry*," Eds. Zorbach W. & Tipson R., Wiley, New York, 1973, vol. 1 & 2.

The 5-nitropyrrolo[2,3-d]pyrimidinyl nucleoside derivatives of the present invention can be synthesized using the methods depicted in Scheme 3 below.

A convergent approach for preparing the pyrrolo[2,3-d] pyrimidinyl nucleosides is shown in Scheme 3 below. First commercially available 4-chloropyrrolo[2,3-d]pyrimidine, compound 11, is coupled to protected 2-methyl substituted sugar 8 (the synthesis of which is described above and by Carroll, et al.,[11,12]) using conditions well known in the art to provide for compound 12. For example, 1-O-methyl-3,5-bis-O-(2,4-dichlorophenylmethyl)-2'-C-methyl-D-ribofuranoside 8 is dissolved in a dry inert solvent, such as dichloromethane, chloroform, carbon tetrachloride and the like, and then the solution is cooled to about 0° C. Afterwards, an excess of HBr or other appropriate reagent, in acetic acid, is added drop wise. This reaction is typically run about 1 to about 4 hours at temperature at about 0 to about 25° C., or until substantially complete as determined by conventional techniques such as TLC. The resulting brominated sugar mixture is isolated and purified using standard techniques such as chromatography, precipitation, crystallization, filtration, and the like. Alternatively, this intermediate may be isolated and used in the next step without further purification.

Preferably, the resulting brominated sugar mixture is co-evaporated, preferably with dry toluene, dissolved in a suitable inert diluent such as dry acetonitrile and stirred with the sodium salt of compound 11 at room temperature over night. The sodium salt of compound 11 is prepared in an inert atmosphere by suspending compound 11 in a dry inert solvent such as, acetonitrile and the like, with NaH dispersed in oil. The reaction is run for about 2 to about 24 hours at a temperature of about 0 to about 40° C. Finally, compound 12 is isolated and purified using standard techniques such as chromatography, precipitation, crystallization, filtration, and the like. Alternatively, this intermediate may be isolated and used in the next step without further purification.

The hydroxyl protecting groups of compound 12 are removed using standard methods to afford compound 13, which is then aminated using methods well known in the art. For example, compound 13 is added to liquid ammonia at about −80° C. and is warmed to about 80° C. for about 24 to about 48 hours to provide for compound 14 which can be isolated and purified using standard techniques such as chromatography, precipitation, crystallization, filtration, and the like or, alternatively, used in the next step without purification and/or isolation.

The hydroxy groups of compound 14 are then protected by acetylation with an excess of acetyl chloride in acetic acid using conventional techniques to provide for compound 15 which can be isolated and purified using standard techniques such as chromatography, precipitation, crystallization, filtration, and the like or, alternatively, used in the next step without purification and/or isolation.

Nitration of compound 15 again occurs under conventional conditions using a mixture of nitric acid ($HNO_3$), and sulfuric acid ($H_2SO_4$), in dichloromethane which provides for compound 16 which can be isolated and purified using standard techniques such as chromatography, precipitation, crystallization, filtration, and the like or, alternatively, used in the next step without purification and/or isolation.

Finally, the acetyl protecting groups on compound 16 are removed under conventional conditions to provide for the 5-nitro derivative, compound 17. This compound can be isolated and purified using standard techniques such as chromatography, precipitation, crystallization, filtration, and the like.

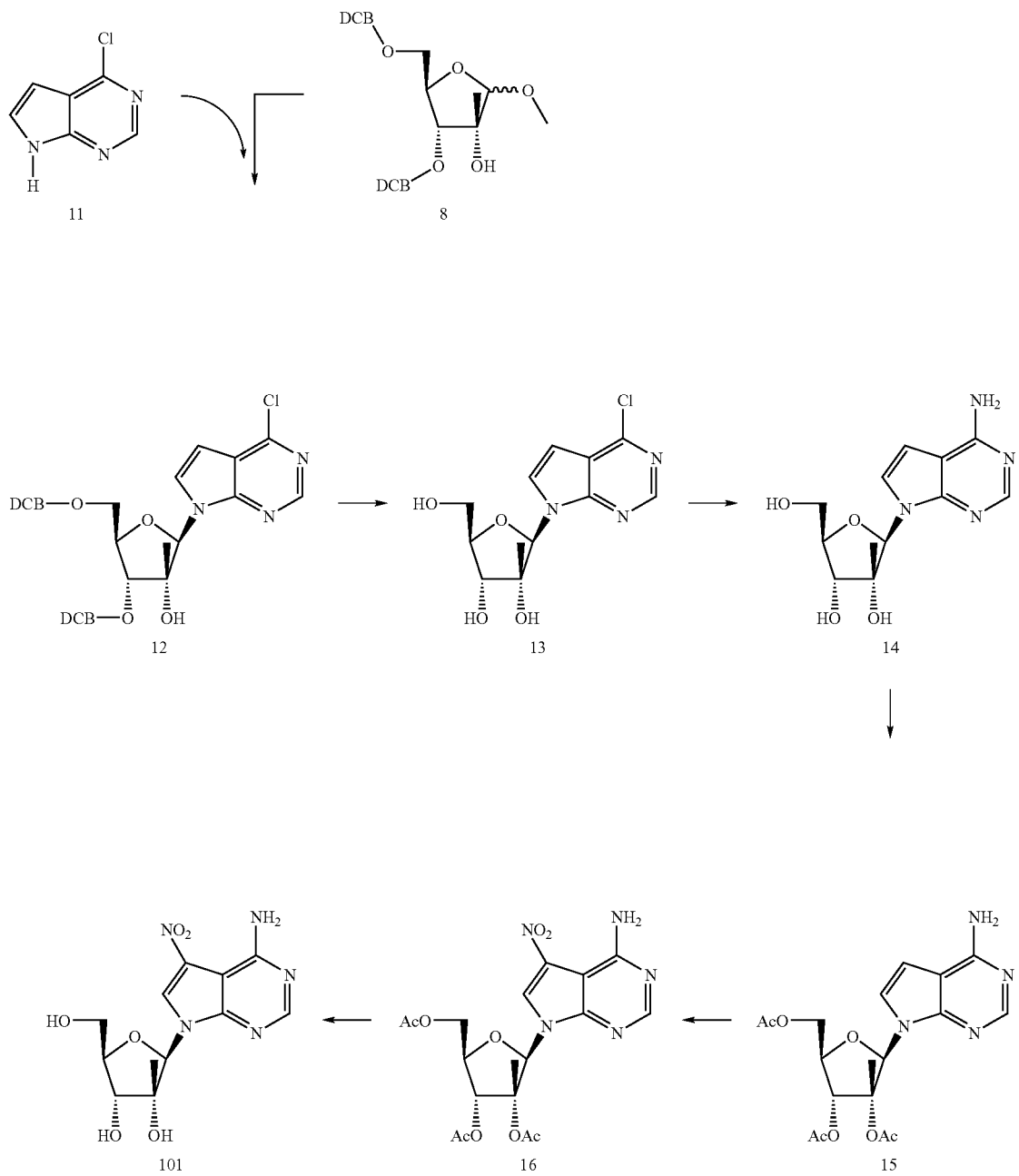

Scheme 3 where DCB is 2,4-dichlorobenzyl and Ac is acetyl

Preparation of compounds where W, $W^1$ or $W^2$ is other than hydrogen, using the compounds prepared in Scheme 3 above as the starting materials, can be accomplished using the methods described in the following reviews of prodrug preparation:
1) Cooperwood, J. S. et al., "*Nucleoside and Nucleotide prodrugs,*" in Ed(s) Chu, C. K. Recent Advances in Nucleosides (2002), 92-147.
2) Zemlicka, J. et al., Biochimica et Biophysica Acta (2002), 158(2-3), 276-286.
3) Wagner, C. et al., Medicinal Research Reviews (2002), 20(6), 417-451.
4) Meier, C. et al., Synlett (1998), (3), 233-242.

For example, conversion of the 5'-hydroxyl group of the 1-[5-(nitro)-4-amino-pyrrolo[2,3-d]pyrimidine]-2'-C-methyl-β-D-ribofuranoside compounds to a phospho, diphospho or triphospho-analog can prepared using the methods describe in D. W. Hutchinson, (Ed. Leroy b. Townsend) "The Synthesis, reaction and Properties of Nucleoside Mono-, Di-, and Triphosphates, and Nucleosides with Changes in the Phosphoryl Residue, "Chemistry of Nucleosides and Nucleotides, Plenum Press, (1991) 2.

The preparation of amino acid esters on the ribofuranoside can be accomplished as shown in Scheme 4 below:

SCHEME 4
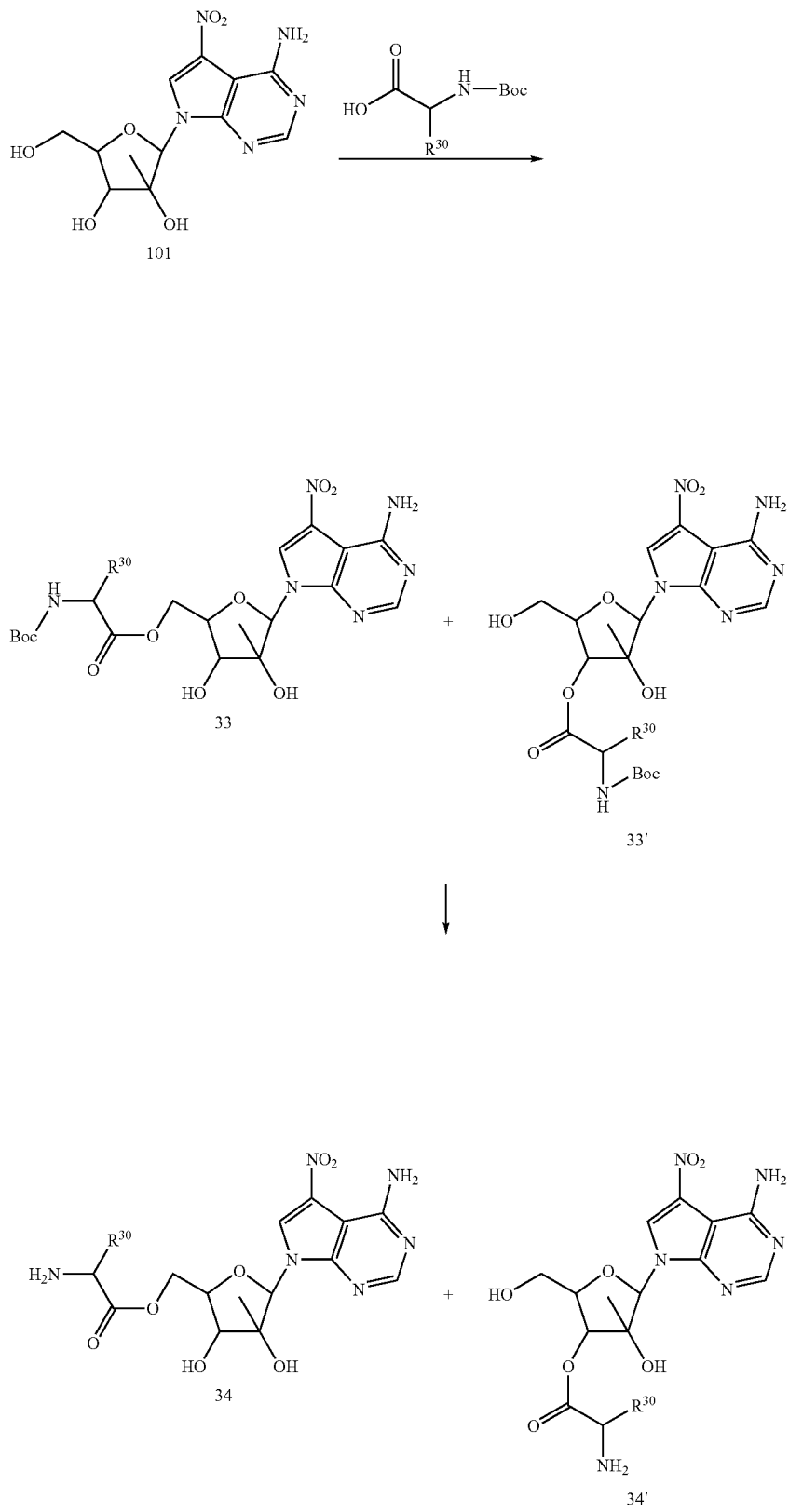

The desired Boc-protected amino acid and N,N'-carbonyldiimidazole are dissolved in an inert solvent such as THF. The reaction mixture is held between about 20 and about 40° C. for about 0.5 to 24 hours. A solution containing an slight excess of the desired nucleoside in an inert solvent such as DMF, is added to the Boc-protected amino acid mixture and is heated at about 40 to about 80° C. for about 2 to about 24 hours. A mixture of structural isomers is isolated and separated using conventional techniques such as evaporation, precipitation, filtration, crystallization, chromatography and the like.

The desired ester is then acidified using, for example, 1:1 v/v TFA/DCM solution for about 0.1 to about 1 hour at about 20 to about 40° C. and evaporated. The residue is dissolved in water and held at about 0 to about 30° C. for about 2 to about 24 hours. The mixture can be separated and the desired product isolated by RP-HPLC using standard techniques and conditions.

While the scheme above demonstrates the production of deazapurine prodrugs, this process can be used on any desired nucleoside compound. Likewise, the amino acid may be protected with any protective group appropriate to the reaction conditions. These protective groups are well known in the art.

techniques such as isolation, crystallization, extraction, filtration, chromatography and the like. Compound 32 is prepared by removing the protecting group at the 5'-position. This can be accomplished by reacting Compound 30 with a 1M solution of tetrabutylammonium fluoride in THF. The final product is isolated and purified using standard techniques such as isolation, crystallization, extraction, filtration, chromatography and the like.

While the scheme above demonstrates the production of deazapurine prodrugs, this process can be used on any desired nucleoside compound.

Utility, Testing, and Administration

Utility

The present invention provides novel compounds possessing antiviral activity, including hepatitis C virus. The compounds of this invention inhibit viral replication by inhibiting the enzymes involved in replication, including RNA dependent RNA polymerase. They may also inhibit other enzymes utilized in the activity or proliferation of viruses in the flaviviridae family, such as HCV.

SCHEME 5

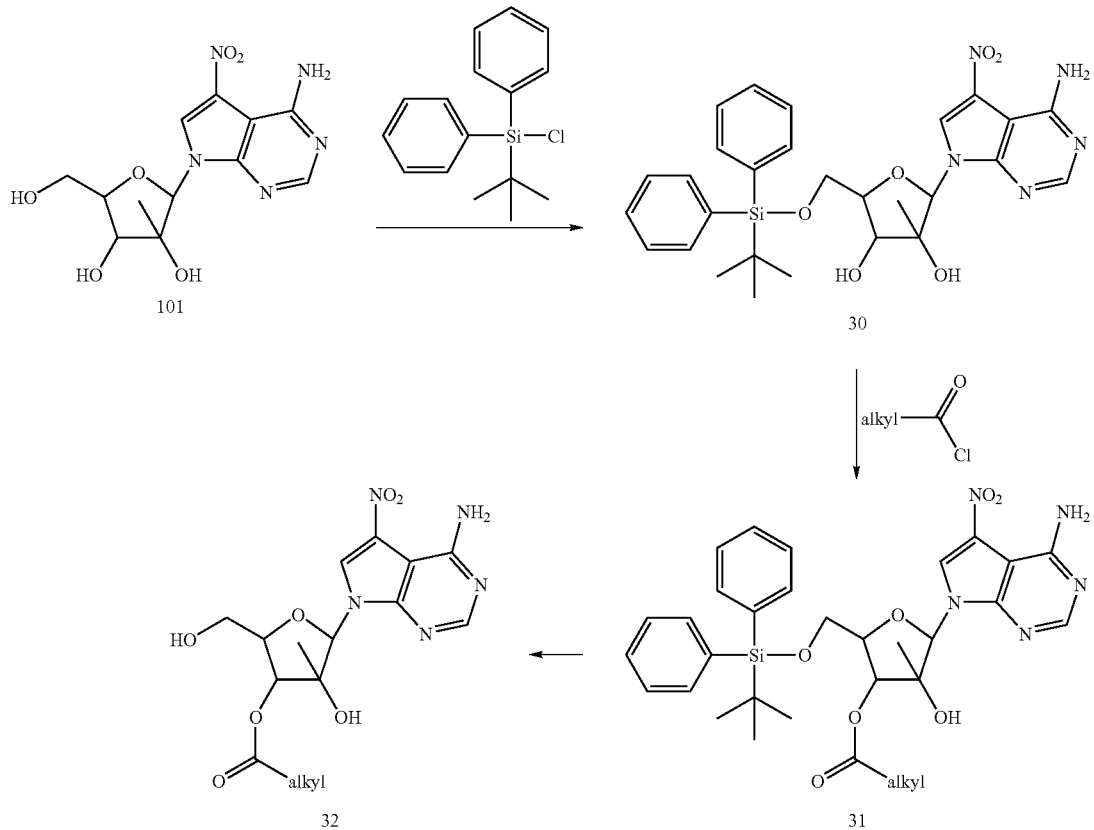

Compound 101 is dissolved in a dry solvent, such as pyridine, and a silylhalide, such as tert-butylchlorodiphenylsilane, is added to form a protecting group at the 5'-position on the sugar. Any protecting group which can be directed to the 5'-position and can be removed orthongally to the final desired 3'-ester can be used. This reaction is run for about 4 to 24 hours at a temperature of about 10 to 40° C. The desired acyl chloride is added to the protected nucleoside, compound 30, and stirred for about 4 to about 24 hours to form compound 31. Which can be isolated and purified using standard The compounds of the present invention can also be used as prodrug nucleosides. As such they are taken up into the cells and can be intracellularly phosphorylated by kinases to the triphosphate and are then inhibitors of the polymerase (NS5b) and/or act as chain-terminators.

Compounds of this invention may be used alone or in combination with other compounds to treat viruses.

Administration and Pharmaceutical Composition

In general, the compounds of this invention will be administered in a therapeutically effective amount by any of the accepted modes of administration for agents that serve similar utilities. The actual amount of the compound of this invention, i.e., the active ingredient, will depend upon numerous factors such as the severity of the disease to be treated, the age and relative health of the subject, the potency of the compound used, the route and form of administration, and other factors. The drug can be administered more than once a day, preferably once or twice a day.

Therapeutically effective amounts of compounds of this invention may range from approximately 0.05 to 50 mg per kilogram body weight of the recipient per day; preferably about 0.01-25 mg/kg/day, more preferably from about 0.5 to 10 mg/kg/day. Thus, for administration to a 70 kg person, the dosage range would most preferably be about 35-700 mg per day.

In general, compounds of this invention will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen that can be adjusted according to the degree of affliction. Compositions can take the form of tablets, pills, capsules, semisolids, powders, sustained release formulations, solutions, suspensions, elixirs, aerosols, or any other appropriate compositions. Another manner for administering compounds of this invention is inhalation.

The choice of formulation depends on various factors such as the mode of drug administration and bioavailability of the drug substance. For delivery via inhalation the compound can be formulated as liquid solution, suspensions, aerosol propellants or dry powder and loaded into a suitable dispenser for administration. There are several types of pharmaceutical inhalation devices—nebulizer inhalers, metered dose inhalers (MDI) and dry powder inhalers (DPI). Nebulizer devices produce a stream of high velocity air that causes the therapeutic agents (which are formulated in a liquid form) to spray as a mist that is carried into the patient's respiratory tract. MDI's typically are formulation packaged with a compressed gas. Upon actuation, the device discharges a measured amount of therapeutic agent by compressed gas, thus affording a reliable method of administering a set amount of agent. DPI dispenses therapeutic agents in the form of a free flowing powder that can be dispersed in the patient's inspiratory airstream during breathing by the device. In order to achieve a free flowing powder, the therapeutic agent is formulated with an excipient such as lactose. A measured amount of the therapeutic agent is stored in a capsule form and is dispensed with each actuation.

Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions may be comprised of a compound of this invention in combination with at least one pharmaceutically acceptable excipient. Acceptable excipients are non-toxic, aid administration, and do not adversely affect the therapeutic benefit of the compound of this invention. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers for injectable solutions, include water, saline, aqueous dextrose, and glycols.

Compressed gases may be used to disperse a compound of this invention in aerosol form. Inert gases suitable for this purpose are nitrogen, carbon dioxide, etc. Other suitable pharmaceutical excipients and their formulations are described in Remington's Pharmaceutical Sciences, edited by E. W. Martin (Mack Publishing Company, 18th ed., 1990).

The amount of the compound in a formulation can vary within the full range employed by those skilled in the art. Typically, the formulation will contain, on a weight percent (wt %) basis, from about 0.01-99.99 wt % of a compound of this invention based on the total formulation, with the balance being one or more suitable pharmaceutical excipients. Preferably, the compound is present at a level of about 1-80 wt %.

Additionally, the present invention is directed to a pharmaceutical composition comprising a therapeutically effective amount of a compound of the present invention in combination with a therapeutically effective amount of another active agent against RNA-dependent RNA virus and, in particular, against HCV. Agents active against HCV include, but are not limited to, Ribavirin, levovirin, viramidine, thymosin alpha-1, an inhibitor of HCV NS3 serine protease, or an inhibitor of inosine monophosphate dehydrogenase, interferon-α, pegylated interferon-α (peginterferon-α), a combination of interferon-α and Ribavirin, a combination of peginterferon-α and Ribavirin, a combination of interferon-α and levovirin, and a combination of peginterferon-α and levovirin. Interferon-α includes, but is not limited to, recombinant interferon-α2a (such as ROFERON interferon available from Hoffman-LaRoche, Nutley, N.J.), interferon-α2b (such as Intron-A interferon available from Schering Corp., Kenilworth, N.J., USA), a consensus interferon, and a purified interferon-α product. For a discussion of Ribavirin and its activity against HCV, see J. O. Saunders and S. A. Raybuck, "Inosine Monophosphate Dehydrogenase: Consideration of Structure, Kinetics and Therapeutic Potential," *Ann. Rep. Med. Chem.*, 35:201-210 (2000).

EXAMPLES

The examples below as well as throughout the application, the following abbreviations have the following meanings. If not defined, the terms have their generally accepted meanings.

AcOH or HOAc=acetic acid $Ac_2O$=acetic anhydride

Boc=t-butoxycarbonyl bs=broad singlet

CAN=ceric ammonium nitrate cm=centimeter d=doublet dd=doublet of doublets
DCC=dicyclohexylcarbodiimide
DCM=dichloromethane
DMEM=Delbecco's minimum eagles medium
DMF=N,N-dimethylformamide
DMSO=dimethylsulfoxide
DTT=dithiothreitol
EDTA=ethylene diamine tetraacetic acid
eq. or eq=equivalents
g=gram
h or hr=hour
HCV=hepatitis C virus
Hz=hertz
IPTG=isopropyl β-D-1-thiogalactopyranoside
IU=international units
kg=kilograms
L=liters
m=multiplet
min=minute
M=molar
mg=milligram
mL=milliliter
mM=millimolar
mmol=millimole
MS=mass spectrum
m/z=mass to charge ratio
ng=nanograms
nm=nanometers
nM=nanomolar
N=normal
NMR=nuclear magnetic resonance
NTP=nucleotide triphosphate
q.s.=quantity sufficient
RP HPLC=reverse phase high performance liquid chromatography
s=singlet
TFA=trifluoroacetic acid
THF=tetrahydrofuran
TLC=thin layer chromatography
$T_m$=melting temperature
UTP=uridine triphosphate
μL=microliters
μg=micrograms
μM=micromolar
v/v=volume to volume
w/w=weight to weight
wt %=weight percent In addition, all reaction temperatures are in degrees Celsius unless reported otherwise.

In the examples below as well as elsewhere throughout this application, the claimed compounds employ the following numbering system:

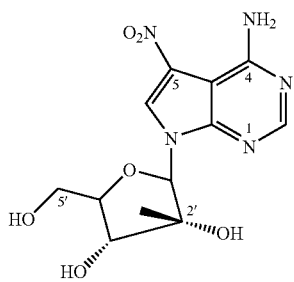

Example 1

Preparation of the intermediate 1-O-methyl-2-methyl-3,5-bis-O-(2,4-dichlorobenzyl)-β-D-ribofuranose

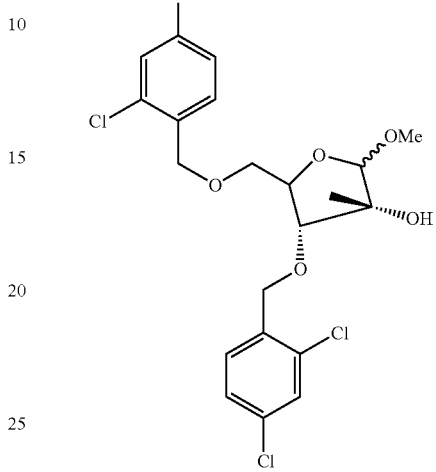

Step 1: Preparation of 1-O-methyl-2,3,5-tris-O-(2,4-dichlorobenzyl)-D-ribofuranose The title compound is synthesized using the methods described in Marin, P.; *Helv. Chim. Acta,* 1995, 78, 486 starting with commercially available D-ribose.

Step 2: Preparation of 1-O-methyl-3,5-bis-O-(2,4-dichlorobenzyl)-D-ribofuranose

To a solution of the product of Step 1 (171.60 g, 0.2676 mol) in 1.8 L of methylene chloride that was cooled to 0° C., was added dropwise a solution of stannous chloride (31.522 mL, 0.2676 mol) in 134 mL of methylene chloride while stirring. After maintaining the solution at about 3° C. for approximately 27 hours, another 5.031 mL of stannous chloride ($SnCl_4$) (0.04282 mol) was added and the solution was kept at about 3° C. overnight. After a total reaction time of approximately 43 hours, the reaction was quenched by carefully adding the solution to 1.9 L of a saturated $NaHCO_3$ solution. Tin salts were removed via filtration through Celite after which the organic phase was isolated, dried with $MgSO_4$ and evaporated in vacuo. The yield of raw, dark yellow oil was 173.6 g. The crude oil was used directly in the next step without further purification.

Step 3: Preparation of 1-O-methyl-2-oxo-3,5-bis-O-(2,4-dichlorobenzyl)-D-ribofuranose To an ice cold solution of Dess-Martin periodinane (106.75 g, 0.2517 mol) in 740 mL anhydrous methylene chloride, under argon, was added a solution of the product of Step 2 above in 662 mL anhydrous methylene chloride over 0.5 hours. The reaction mixture was stirred at 0° C. for 0.5 hours and then at room temperature for 6 days. The mixture was diluted with 1.26 L of anhydrous diethyl ether and then poured into an ice-cold mixture of $Na_2S_3O_3.5H_2O$ (241.2 g, 1.5258 mol) in 4.7 L of saturated aqueous sodium bicarbonate. The layers were separated, and the organic layer was washed with 1.3 L of saturated aqueous sodium bicarbonate, 1.7 L water and 1.3 L brine, dried with $MgSO_4$, filtered and evaporated to give the target compound. The compound (72.38 g, 0.1507 mol) was used without further purification in the next step.

Step 4: Preparation of the Title Compound

A solution of MeMgBr in 500 mL anhydrous diethyl ether was added dropwise to a solution of the product of step 3 above (72.38 g, 0.1507 mol) at −55° C. also in 502 mL of anhydrous diethyl ether. The reaction mixture was allowed to warm to −30° C. and stirred mechanically for 4 hours at about −30° C. to about −15° C., then poured into 2 L ice cold water. After stirring vigorously at ambient temperature for 0.5 hours, the mixture was filtered through a Celite pad (14×5 cm), which was thoroughly washed with diethyl ether. The organic layer was dried with MgSO$_4$, filtered and concentrated in vacuo. The residue was dissolved in hexanes (~1 mL per gram crude), applied to a silica gel column (1.5 L silica gel in hexanes) and eluted with hexanes and 4:1 hexanes:ethyl acetate (v/v) to give 53.58 g (0.1080 mol) of the final purified product. The morphology of the title compound was that of an off-yellow, viscous oil;

MS: m/z 514.06 (M+NH$_4$+).

Example 2

Preparation of 7-(2'-C-methyl-β-D-ribofuranosyl)-4-amino-5-nitro-pyrrolo[2,3-d]pyrimidine (Compound 101)

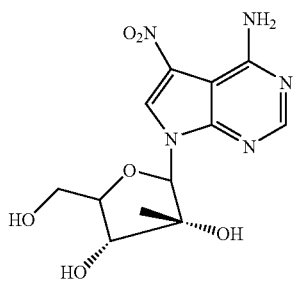

Step 1. Synthesis of 7-(2'-methyl-3',5'-di(-O-2,4-dichlorobenzyl)-β-D-ribofuranosyl)-4-chloro-pyrrolo[2,3-d]pyrimidine 4-Chloro-7H-pyrrolo[2,3-d]pyrimidine (10.0 g, 65.11 mmol) (Toronto Research) was suspended in 1.3 liters of dry acetonitrile and NaH (2.6 g, 65.11 mmol, 60% dispersion in oil) was added and the mixture was stirred for 4 hours at ambient temperature under argon. Meanwhile, 1-O-methyl-3,5-bis-O-(2,4-dichlorobenzyl)-2'-methyl-D-ribofuranoside (12.8 g, 25.79 mmol) was dissolved in 284 mL of dry dichloromethane, cooled down to 0° C. and HBr (28 mL, 30% w/w in AcOH) was added drop wise over 30 minutes. The reaction was kept for 1 hour at 0° C. and 3.0 hours more at ambient temperature then evaporated. The mixture was 3 times co-evaporated with dry toluene, dissolved in dry acetonitrile (200 mL) and added to the sodium salt of the base. The reaction mixture was kept at room temperature over night and evaporated to dryness. The residue was taken up in ethyl acetate (500 mL) and washed with water (3×100 mL). The organic fraction was dried over sodium sulfate, evaporated, and the crude material was purified by flash chromatography on silica gel (ethyl acetate/dichloromethane 5:100 v/v) to yield 10.0 g (63%) of protected nucleoside;

MS: 617.75 (M+1); H NMR (CDCl$_3$): δ 8.64 (s, 1H), 7.68 (d, 1H, J=3.6 Hz), 7.5-7.1 (m, 6H), 6.56 (d, 1H, 3.6 Hz), 6.4 (s, 1H), 4.8-4.5 (m, 4H), 4.3-3.65 (m, 4H), 0.93 (s, 3H).

Step 2. Synthesis of 7-(2'-methyl-β-D-ribofuranosyl)-4-chloro-pyrrolo[2,3-d]pyrimidine To the solution of the product from Step 1 (10.0 g, 16.19 mmol) in dichloromethane (440 mL) at −78° C. was added boron trichloride (1M in dichloromethane) (157 mL, 157.0 mmol) dropwise over 30 minutes. The mixture was stirred at −78° C. for 2 hours then at −20° C. overnight. The reaction was quenched with dichloromethane/methanol 1:1 (420 mL) and neutralized at 0° C. with aqueous ammonia. The solid was filtered, washed with dichloromethane/methanol 1:1 and the combined extracts evaporated in vacuo. The residue was purified on silica gel column with dichloromethane/methanol (10:1 v/v) as eluent. Fractions containing product were combined and concentrated to yield 4.1 g (84%) of the deprotected nucleoside;

MS: 300.08 (M+1); $^1$H NMR (D$_2$O): δ 8.32 (s, 1H), 7.57 (d, 1H, J=3.6 Hz), 6.56 (d, 1H, J=3.6 Hz), 6.17 (s, 1H), 4.0-3.5 (m, 4H), 0.65 (s, 3H).

Step 3. Synthesis of 7-(2'-methyl-β-D-ribofuranosyl)-4-amino-pyrrolo[2,3-d]pyrimidine The product from Step 2 (1.1 g, 3.68 mmol) was placed in an autoclave pressure bomb and liquid ammonia was added (10 mL) at −78° C. The vessel was sealed and heated to 85° C. for 24 hours. The vessel was cooled back to −78° C., opened and the ammonia was allowed to evaporate. The residue was taken up in a small amount of methanol and plated onto a glass filter column containing a small pad of silica gel. The methanol was allowed to evaporate under vacuum and the product was eluded by ramping to 20% methanol in dichloromethane to give 1.0 g (97%) of a light yellow powder;

$^1$H NMR (CD$_3$OD): δ 8.06 (s, 1H), 7.48 (d, 1H, J=3.6 Hz), 6.60 (d, 1H, J=3.6 Hz), 6.21 (s, 1H), 4.13-3.85 (m, 4H), 0.81 (s, 3H); MS: 281.14 (M+1).

Step 4. Synthesis of 7-(2'-methyl-2',3',5'-tri(-O-acetyl)-β-D-ribofuranosyl)-4-amino-pyrrolo[2,3-d]pyrimidine To a solution of the product from Step 3 (1.10 g, 3.92 mmol) in glacial acetic acid (8 mL) was added acetyl chloride (3 mL) and the mixture stirred at room temp overnight. The reaction was concentrated in vacuo and the residue was plated onto silica gel column with dichloromethane and eluded by ramping to 5% methanol in dichloromethane to give 1.5 g (94%); MS 407.18 (M+1).

Step 5. Synthesis of 7-(2'-methyl-2',3',5'-tri(-O-acetyl)-β-D-ribofuranosyl)-4-amino-5-nitro-pyrrolo[2,3-d]pyrimidine A solution of the product from Step 4 (1.5 g, 3.69 mmol) in dichloromethane (25 mL) was cooled to 0° C. and a 1:1 mixture of fuming nitric acid and sulfuric acid (4 mL) was added dropwise and the reaction was vigorously stirred at 0° C. for 20 min. The reaction was quenched with ice cold saturated sodium bicarbonate solution. The quenched reaction was diluted with water and extracted with dichloromethane. The organic layer was dried over sodium sulfate and concentrated in vacuo. The residue was purified by plating on silica gel with dichloromethane and eluded by ramping to 5% methanol in dichloromethane to give 600 mg (36%);

MS: 452.16 (M+1).

Step 6. Synthesis of 7-(2'-methyl-β-D-ribofuranosyl)-4-amino-5-nitro-pyrrolo[2,3-d]pyrimidine To the product from Step 5 (400 mg, 0.886 mmol) was added 7 N NH$_3$ in methanol (15 mL) and stirred at room temp for 1.5 hours. The reaction was concentrated in vacuo and the residue was purified on reverse phase HPLC using a gradient of 0-35% buffer B over 30 min at a rate of 10 mL/min (Buffer A=H$_2$O; Buffer B=acetonitrile). The product was then crystallized from ethanol to give 70 mg (24%);

$^1$H-NMR (DMSO-d6): δ 9.14 (s, 1H), 8.23 (s, 1H), 7.86 (bs, 1H), 7.23 (bs, 1H), 6.16 (s, 1H), 5.50 (dd, 1H), 5.37 (s,

1H), 5.22 (d, 1H), 3.99-3.67 (m, 4H), 0.79 (s, 3H); MS: 326.1 (M+1); Karl Fischer: <0.1% water; Elemental analysis: C=44.40% H=4.41% N=21.48%.

Example 3

Preparation of 7-(2'-C-methyl-5'-triphospho-β-D-ribofuranosyl)-4-amino-5-nitro-pyrrolo[2,3-d]pyrimidine (Compound 104)

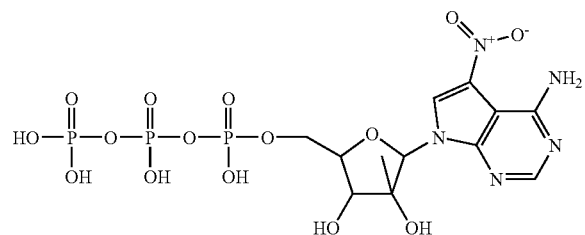

Compound 101 (57 mg, 1.5 mmol)) was dried by co-evaporation with dry pyridine (2×5 mL) and toluene (2×5 mL) and suspended in trimethylphosphate (5 mL). Phosphoro oxychloride (1.2 eq.) was added and reaction mixture kept for 2 h at 5° C. Tributylammonium pyrophosphate (1 mL of 2N solution in DMF) was added and the mixture was left overnight at 5° C. Reaction was quenched with $Et_3NHCO_3$ buffer and separated by RP-HPLC from 0 to 100% B, buffer A—water, buffer B—$CH_3CN$. The major peak was collected, concentrated and repurified by RP-HPLC from 0 to 60% B. Buffers were as mentioned above. The major peak was collected and lyophilized;

MS 563.99 (M−1); $^{31}$P-NMR ($D_2O$): −4.44 (d, 1P, P-α), −9.85 (d, 1P, P-γ), −19.83 (t, 1P, P-β); $^1$H-NMR ($D_2O$): 8.40 (s, 1H, base), 8.03 (s, 1H, base), 6.19 (s, 1H, H-1'), 4.25-4.10 (m, 4H, H-3', H-4' & H-5'a,b), 0.78 (s, 3H, $CH_3$).

Comparative Example A

Preparation of 7-(2'-methyl-β-D-ribofuranosyl)-4-amino-5-carboxy-pyrrolo[2,3-d]pyrimidine

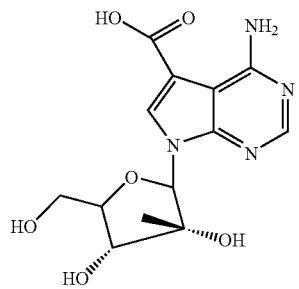

The synthesis of the title compound is found in the International Patent Publication Number WO 02/057425 at least on page 162.

Biological Examples

Example 1

Anti-Hepatitis C Activity

Compounds can exhibit anti-hepatitis C activity by inhibiting HCV polymerase, by inhibiting other enzymes needed in the replication cycle, or by other pathways. A number of assays have been published to assess these activities. A general method that assesses the gross increase of HCV virus in culture is disclosed in U.S. Pat. No. 5,738,985 to Miles et al. In vitro assays have been reported in Ferrari et al. *Jnl. of Vir.*, 73:1649-1654, 1999; Ishii et al., *Hepatology*, 29:1227-1235, 1999; Lohmann et al., *Jnl of Bio. Chem.*, 274:10807-10815, 1999; and Yamashita et al., *Jnl. of Bio. Chem.*, 273:15479-15486, 1998.

WO 97/12033, filed on Sep. 27, 1996, by Emory University, listing C. Hagedorn and A. Reinoldus as inventors, which claims priority to U.S. Provisional Patent Application Ser. No. 60/004,383, filed on September 1995, describes an HCV polymerase assay that can be used to evaluate the activity of the of the compounds described herein. Another HCV polymerase assay has been reported by Bartholomeusz, et al., Hepatitis C Virus (HCV) RNA polymerase assay using cloned HCV non-structural proteins; Antiviral Therapy 1996: 1(Supp 4) 18-24.

Screens that measure reductions in kinase activity from HCV drugs are disclosed in U.S. Pat. No. 6,030,785, to Katze et al., U.S. Pat. No. 6,228,576, Delvecchio, and U.S. Pat. No. 5,759,795 to Jubin et al. Screens that measure the protease inhibiting activity of proposed HCV drugs are disclosed in U.S. Pat. No. 5,861,267 to Su et al., U.S. Pat. No. 5,739,002 to De Francesco et al., and U.S. Pat. No. 5,597,691 to Houghton et al.

Example 2

Replicon Assay

A cell line, ET (Huh-lucubineo-ET) is used for screening of compounds of the present invention for HCV RNA dependent RNA polymerase. The ET cell line is stably transfected with RNA transcripts harboring a $I_{389}$luc-ubi-neo/NS3-3'/ET; replicon with firefly luciferase-ubiquitin-neomycin phosphotransferase fusion protein and EMCV-IRES driven NS3-5B polyprotein containing the cell culture adaptive mutations (E1202G; T1280I; K1846T) (Krieger at al, 2001 and unpublished). The ET cells are grown in DMEM, supplemented with 10% fetal calf serum, 2 mM Glutamine, Penicillin (100 IU/mL)/Streptomycin (100 µg/mL), 1× nonessential amino acids, and 250 µg/mL G418 ("Geneticin"). They are all available through Life Technologies (Bethesda, Md.). The cells are plated at 0.5-1.0×$10^4$ cells/well in the 96 well plates and incubated for 24 hrs before adding nucleoside analogs. Then the compounds were added to the cells to achieve a final desired concentration (i.e.: 5 or 50 µM). Luciferase activity will be measured 48-72 hours later by adding a lysis buffer and the substrate (Catalog number Glo-lysis buffer E2661 and Bright-Glo leuciferase system E2620 Promega, Madison, Wis.). Cells should not be too confluent during the assay. Percent inhibition of replication will be plotted relative to no compound control. Under the same condition, cytotoxicity of the compounds will be determined using cell proliferation reagent, WST-1 (Roche, Germany). The compounds showing antiviral activities, but no significant cytotoxicities will be chosen to determine $IC_{50}$ and $TC_{50}$. For these determinations, 6 dilutions of each compound were used. Compounds were typically diluted 3 fold to span a concentration range of 250 fold. $IC_{50}$ and $TC_{50}$ values were calculated by fitting % inhibition at each concentration to the following equation:

% inhibition=100%/[($IC50/[I])^b$+1]

where b is Hill's coefficient.

Example 3

Cloning and Expression of Recombinant HCV-NS5b

The coding sequence of NS5b protein is cloned by PCR from pFKI$_{389}$luc/NS3-3'/ET as described by Lohmann, V., et al. (1999) *Science* 285, 110-113 using the following primers:

aggacatggatccgcggggtcgggcacgagacag (SEQ. ID. NO. 1)

aaggctggcatgcactcaatgtcctacacatggac (SEQ. ID. NO. 2)

The cloned fragment is missing the C terminus 21 amino acid residues. The cloned fragment is inserted into an IPTG-inducible expression plasmid that provides an epitope tag (His)6 at the carboxy terminus of the protein.

The recombinant enzyme is expressed in XL-1 cells and after induction of expression, the protein is purified using affinity chromatography on a nickel-NTA column. Storage condition is 10 mM Tris-HCl pH 7.5, 50 mM NaCl, 0.1 mM EDTA, 1 mM DTT, 20% glycerol at −20° C.

Example 4

HCV-NS5b Enzyme Assay

The polymerase activity is assayed by measuring incorporation of radiolabeled UTP into a RNA product using a biotinylated, heteropolymeric template, which includes a portion of the HCV genome. Typically, the assay mixture (50 μL) contains 10 mM Tris-HCl (pH 7.5), 5 mM MgCl$_2$, 0.2 mM EDTA, 10 mM KCl, 1 unit/μL RNAsin, 1 mM DTT, 10 μM each of NTP, including [$^3$H]-UTP, and 10 ng/μL heteropolymeric template. Test compounds are initially dissolved in 100% DMSO and further diluted in aqueous buffer containing 5% DMSO. Typically, compounds are tested at concentrations between 1 nM and 100 μM. Reactions are started with addition of enzyme and allowed to continue at 37° C. for 2 hours. Reactions are quenched with 8 μL of 100 mM EDTA and reaction mixtures (30 μL) are transferred to streptavidin-coated scintillation proximity microtiter plates (FlashPlates) and incubated at 4° C. overnight. Incorporation of radioactivity is determined by scintillation counting.

Activity Results

Table II shows the assay results for some compounds of this invention.

TABLE II

|  | Replicon Assay | NS5b Assay |
|---|---|---|
| Compound 101 | 0.06 μm |  |
| Compound 104 |  | 2.6 μm |
| Comparative Example A | >50 μm |  |

Formulation Examples

The following are representative pharmaceutical formulations containing a compound of the present invention.

Example 1

Tablet Formulation

The following ingredients are mixed intimately and pressed into single scored tablets.

| Ingredient | Quantity per tablet, mg |
|---|---|
| compound of this invention | 400 |
| cornstarch | 50 |
| croscarmellose sodium | 25 |
| lactose | 120 |
| magnesium stearate | 5 |

Example 2
Capsule Formulation

The following ingredients are mixed intimately and loaded into a hard-shell gelatin capsule.

| Ingredient | Quantity per capsule, mg |
|---|---|
| compound of this invention | 200 |
| lactose, spray-dried | 148 |
| magnesium stearate | 2 |

Example 3

Suspension Formulation

The following ingredients are mixed to form a suspension for oral administration.

| Ingredient | Amount |
|---|---|
| compound of this invention | 1.0 g |
| fumaric acid | 0.5 g |
| sodium chloride | 2.0 g |
| methyl paraben | 0.15 g |
| propyl paraben | 0.05 g |
| granulated sugar | 25.0 g |
| sorbitol (70% solution) | 13.00 g |
| Veegum K (Vanderbilt Co.) | 1.0 g |
| flavoring | 0.035 mL |
| colorings | 0.5 mg |
| distilled water | q.s. to 100 mL |

Example 4
Injectable Formulation

The following ingredients are mixed to form an injectable formulation.

| Ingredient | Amount |
|---|---|
| compound of this invention | 0.2 mg-20 mg |
| sodium acetate buffer solution, 0.4 M | 2.0 mL |
| HCl (1N) or NaOH (1N) | q.s. to suitable pH |
| water (distilled, sterile) | q.s. to 20 mL |

Example 5

Suppository Formulation

A suppository of total weight 2.5 g is prepared by mixing the compound of the invention with Witepsol® H-15 (triglycerides of saturated vegetable fatty acid; Riches-Nelson, Inc., New York), and has the following composition:

| Ingredient | Amount |
|---|---|
| compound of the invention | 500 mg |
| Witepsol ® H-15 | balance |

What is claimed is:

1. A compound selected from the group consisting of:
  7-(2'-C-methyl-β-D-ribofuranosyl)-4-amino-5-nitro-pyrrolo[2,3-d]pyrimidine;
  7-(2'-C-methyl-5'-phospho-β-D-ribofuranosyl)-4-amino-5-nitro-pyrrolo[2,3-d]pyrimidine;
  7-(2'-C-methyl-5'-diphospho-β-D-ribofuranosyl)-4-amino-5-nitro-pyrrolo[2,3-d]pyrimidine; and
  7-(2'-C-methyl-5'-triphospho-β-D-ribofuranosyl)-4-amino-5-nitro-pyrrolo[2,3-d]pyrimidine.

2. A pharmaceutical composition comprising a pharmaceutically acceptable diluent and a therapeutically effective amount of a compound according to claim 1.

3. A method for treating a viral infection mediated at least in part by a virus of the flaviviridae family of viruses in a mammal, which method comprises administering to a mammal that has been diagnosed with said viral infection a pharmaceutical composition according to claim 2, wherein said virus is hepatitis C virus (HCV).

* * * * *

SEQUENCE LISTING

<160> NUMBER OF SEQ ID NOS: 2

<210> SEQ ID NO 1
<211> LENGTH: 34
<212> TYPE: DNA
<213> ORGANISM: Artificial
<220> FEATURE:
<223> OTHER INFORMATION: Synthetic Primer

<400> SEQUENCE: 1
aggacatgga tccgcggggt cgggcacgag acag     34

<210> SEQ ID NO 2
<211> LENGTH: 35
<212> TYPE: DNA
<213> ORGANISM: Artificial
<220> FEATURE:
<223> OTHER INFORMATION: Synthetic Primer

<400> SEQUENCE: 2
aaggctggca tgcactcaat gtcctacaca tggac     35